United States Patent [19]
Opie et al.

[11] Patent Number: 4,825,850
[45] Date of Patent: May 2, 1989

[54] CONTAMINATION PROTECTION SYSTEM FOR ENDOSCOPE CONTROL HANDLES

[75] Inventors: Eric Opie, Brier; Fred E. Silverstein, Seattle, both of Wash.

[73] Assignee: Opielab, Inc., Seattle, Wash.

[21] Appl. No.: 193,833

[22] Filed: May 13, 1988

[51] Int. Cl.⁴ .............................................. A61B 1/00
[52] U.S. Cl. ........................................................ 128/4
[58] Field of Search ........................... 128/4, 6, 11, 23

[56] References Cited

U.S. PATENT DOCUMENTS

| | | | |
|---|---|---|---|
| 3,426,749 | 2/1969 | Jephcott | 128/11 |
| 3,794,091 | 2/1974 | Ersek et al. | 128/23 X |
| 3,809,072 | 5/1974 | Ersek et al. | 128/23 |
| 4,461,282 | 7/1984 | Ouchi et al. | 128/4 |
| 4,646,722 | 3/1987 | Silverstein et al. | 128/4 |
| 4,741,326 | 5/1988 | Sidell et al. | 128/4 |
| 4,742,816 | 5/1988 | Suzuki et al. | 128/4 |

*Primary Examiner*—William H. Grieb
*Attorney, Agent, or Firm*—Seed and Berry

[57] ABSTRACT

A contamination system for endoscopes having a handle, an insertion tube projecting from the handle, and control knobs detachably mounted on control shafts projecting from the handle to control the angular orientation of distal end of the insertion tube. The handle is placed in a liquid-impermeable bag, with the control shafts projecting through an aperture in the bag. The control knobs are then attached to the shafts prior to performing an endoscopic procedure. After the procedure has been completed, the control knobs are removed from the shafts and decontaminated, the handle is removed from the bag, and the bag is discarded.

18 Claims, 8 Drawing Sheets

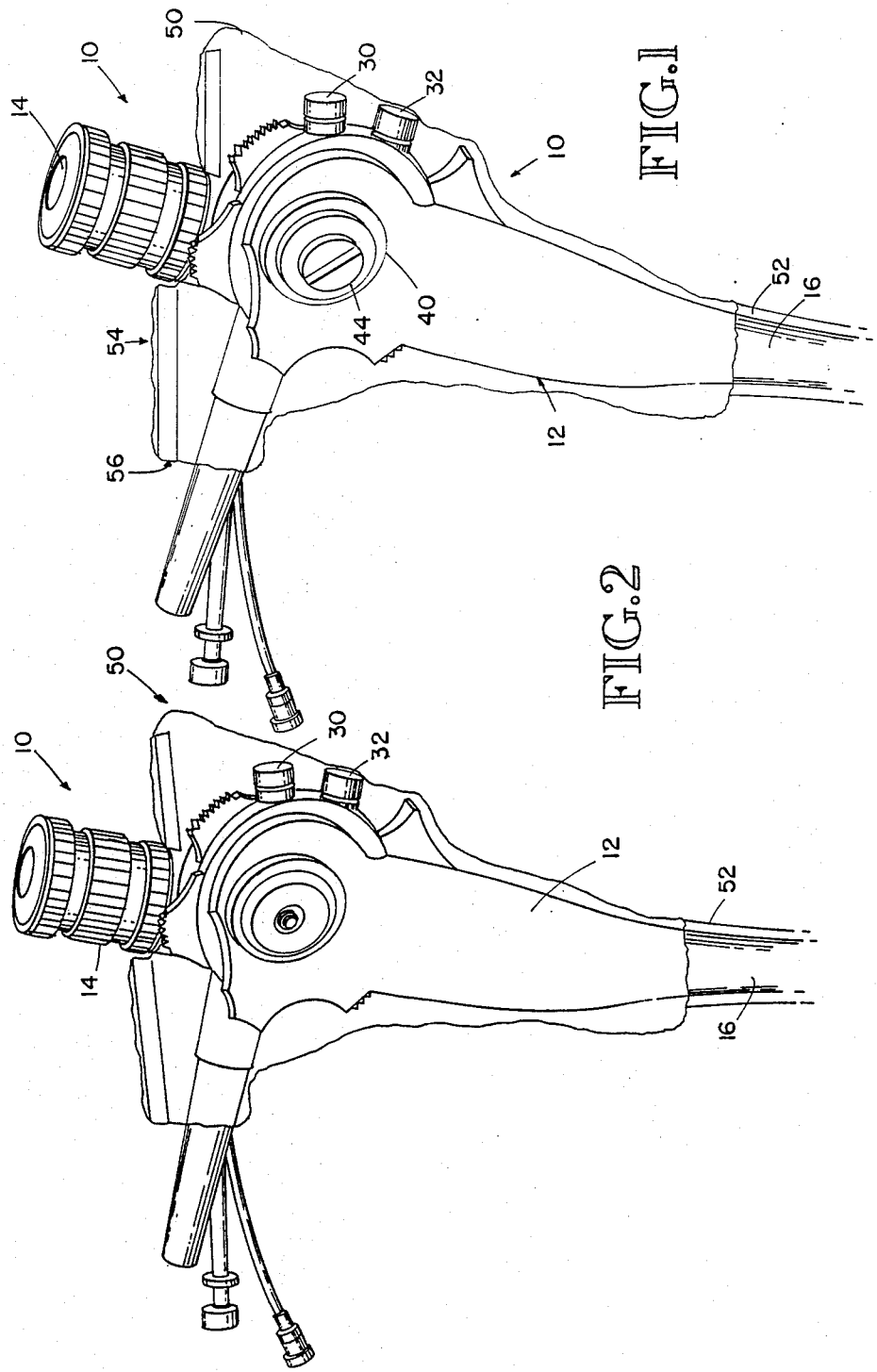

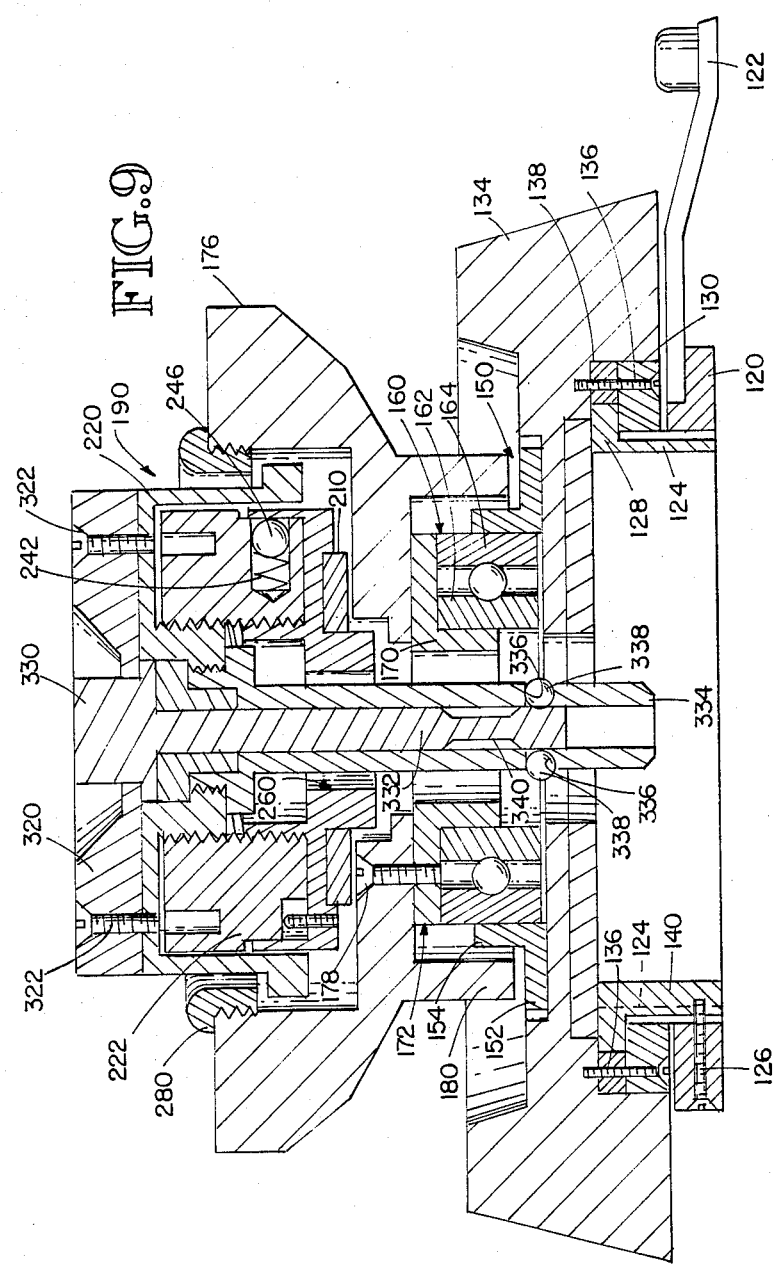

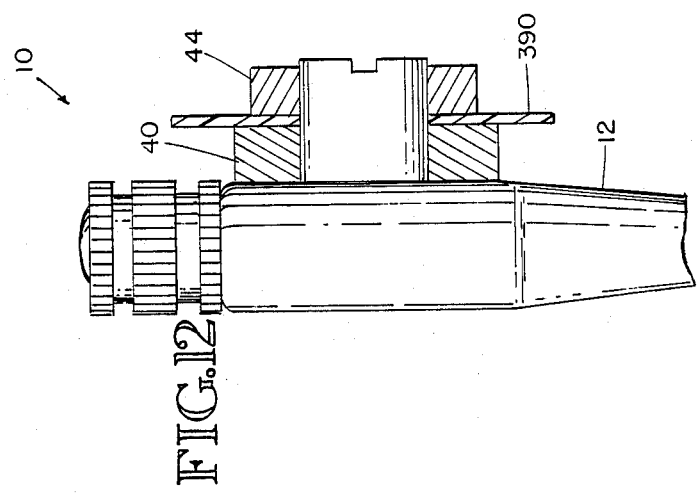
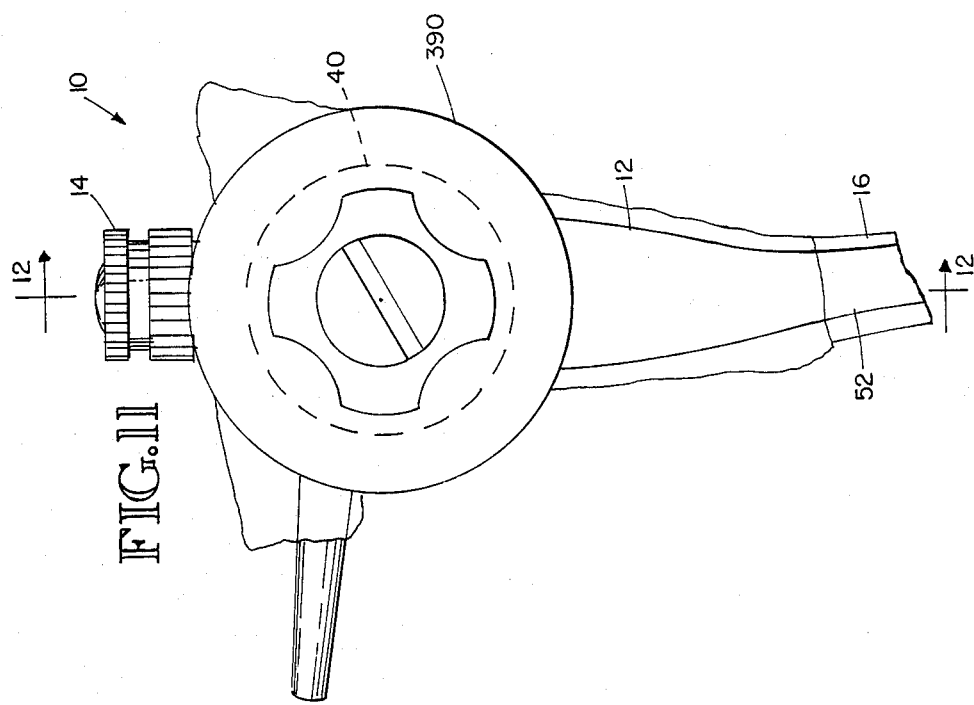

CONTAMINATION PROTECTION SYSTEM FOR ENDOSCOPE CONTROL HANDLES

DESCRIPTION

1. Field of the Invention

This invention relates to the field of endoscopy, and more particularly, to a system for isolating an endoscope from viruses and bacteria during use.

2. Background Art

The use of endoscopes for diagnostic and therapeutic indications is rapidly expanding. To improve performance, endoscopes have been optimized to best accomplish their purpose. Therefore, there are upper endoscopes for examination of the esophagus, stomach and duodenum; colonoscopes for examining the colon; angioscopes for examining blood vessels; bronchoscopes for examining the bronchi; laparoscopes for examining the peritoneal cavity; and arthroscopes for examining joint spaces. The discussion which follows will apply to all of these types of endoscopes.

Instruments to examine the rectum and sigmoid colon, known as flexible sigmoidoscopes, are good examples of the usefulness of endoscopic technology. These devices are expensive, and they are used in a contaminated environment for a procedure which is brief (5–10 minutes) and where problems of cleaning time and contamination are important factors. There has been a large increase in the use of the "flexible sigmoidoscope" for use in screening symptomatic and asymptomatic patients for colon and rectal cancer. Ideally, flexible sigmoidoscopes must be used rapidly and inexpensively in order to maintain the cost of such screening at acceptable levels. Typically, a clinic would like to perform five sigmoidoscope examinations each hour. A significant problem with making such examinations quick and inexpensive is the time necessary for adequately cleaning the device.

Although endoscopes can be superficially cleaned in two to four minutes, this relatively cursory cleaning may not be adequate for complete disinfection or sterilization. Even a more complete cleaning requiring on the order of eight to ten minutes may not allow adequate cleaning, particularly in view of the increasing problems with contagious viruses. Even with the use of chemicals such as gluteraldehyde, depending on cleaning methods, adequate cleanliness may not be possible.

The cleaning problem not only includes the outside of the endoscope, but also the multiple small channels inside the endoscope. This includes channels for: air insufflation; water to wash the tip; and biopsy and suction. Each channel also has a control valve. The channels extend along the length of the endoscope and come into contact with body tissues and fluids. It is extremely difficult to adequately clean these channels even when skilled health practitioners spend a great deal of time on the cleaning procedure.

Even if endoscopes can be adequately cleaned in eight to ten minutes, the cleaning still prevents endoscopy examinations from being relatively inexpensive. While a physician may spend five to ten minutes performing some types of endoscopy, he or she will generally waste a great deal of time waiting for the endoscope to be cleaned before he or she can conduct another endoscopy. A partial solution to the "idle time" problem is to purchase multiple instruments so one can be used as the others are being cleaned. However, the expense of having duplicate endoscopes of each of the many types described above makes this solution impractical especially for physicians' offices and smaller clinics.

Not only must the idle time of the physician be added to the cost of endoscopic examinations, but the time spent by a nurse or other hospital personnel in the cleaning as well as the cost of disinfecting chemicals and other costs of the cleaning process must also be added to the cost of the examination. Although automatic washing machines are available to clean endoscopes, these machines are expensive, take up significant amounts of space, are noisy and are not faster than washing by hand. Further, regardless of whether the cleaning is done manually or by machine, the cleaning chemicals can be harmful to the endoscope and thus significantly shorten its life. The cleaning chemicals, being toxic, are also potentially injurious to the staff who use them, and to the environment into which they are discharged. To use some of these chemicals safely, such as gluteraldehyde, requires a dedicated ventilated hood, which uses up space and is expensive to install and operate. The chemicals are also potentially toxic to the patient in that, if residue remains after cleaning and rinsing the instrument, the patient could have a reaction to the chemicals.

As a result of these many problems, conventional endoscope cleaning techniques increase the cost of endoscopic procedures. Furthermore, while the risk of contamination using endoscopes is often far less than the risk of alternative procedures, such as surgery, there is nevertheless a risk that endoscopes are not adequately cleaned to prevent the risk of transmission of infectious diseases from one patient to the next.

In the health care field, the problems of contaminated instruments transmitting disease from one patient to the next have generally been solved by making such instruments disposable. However, this approach has not been thought possible in the field of endoscopy because endoscopes are very expensive instruments. Moreover, it has not been thought possible to isolate the endoscope from the patient or the external environment because the endoscope itself has channels inside it that are used as a conduit for body fluids and tissues, such as, for example, in taking biopsies. The only method currently available to actually sterilize an endoscope is to use gas sterilization with ethylene oxide gas. However, there are several disadvantages in using this procedure. The procedure is very slow (up to 24 hours) during which the endoscope cannot be used. Also, the gas affects the plastic of the endoscope and may limit its life span. Finally, the gas is toxic, and, therefore, great care must be taken to ensure that no residue remains that might cause patient or staff, irritation or allergic reaction during contact with the endoscope.

As a result of the above-described limitations in using and cleaning endoscopes by conventional techniques, there has not heretofore been an acceptable solution to the problem of making endoscopy procedures both inexpensive and entirely safe.

A new approach to the problem of endoscope contamination is described in U.S. Pat. No. 4,646,722. This new approach involves the use of an endoscope sheath having a flexible tube surrounding the elongated core of an endoscope. The flexible tube has a transparent window near its distal end positioned in front of the viewing window of the endoscope. Channels that come into contact with the patient or the patient's body fluids, e.g.

channels for taking biopsies, injecting air or injecting water to wash the window of the sheath, extend along the endoscope, either inside or outside the sheath. Where the channels are positioned inside the sheath, they may be inserted in a longitudinal groove formed in the endoscope core. The protective sheath may be used with either end-viewing endoscopes or side-viewing endoscopes. The protective sheath may be installed by rolling the elastomeric tube into an annular configuration and then unrolling the tube over the core of the endoscope. Alternatively, the tube may be inflated in its unrolled configuration to expand the tube and allow it to be easily slipped onto the endoscope core. A variety of specialized endoscopes may be created by using protective sheaths having a variety of special purpose medical instruments mounted at the end of a biopsy channel and operated through the channel.

The endoscope used in the implementation of the above described concept in one configuration must have a groove formed along its length. A tube is inserted into this groove to provide channels for air, water and suction. Once the groove is inserted, it is covered with the sheath. After use, the sheath and channel insert are removed and disposed of, leaving the endoscope free of contamination resulting from the endoscopic procedure.

The sheath concept covers the insertion tube of the endoscope and allows for the disposal of this sheath and the channels which are incorporated into the sheath insert: air channel; water channel; and suction/biopsy channel. However, there is still a problem with the control handle of the endoscope. The way endoscopes are used clinically is that the control body of the instrument is held in the endoscopist's left hand. The right hand is usually placed on the endoscope's shaft to advance the instrument into the patient and to pull the instrument out of the patient. This results in contamination of the right hand with patient secretions including blood, mucus, stool, and tissue. This contamination occurs during every endoscopic procedure. The endoscopist wears gloves to protect his or her hand. However, during the procedure, the endoscopist frequently must reach up with his or her right hand and move the endoscope control wheels. These two wheels control up/down and right/left movement of the controllable tip bending section of the endoscope. Although it is possible to control these wheels somewhat with the left hand, it is often essential to reach up with the right hand to assist with a complex control movement. This results in the immediate contamination of the endoscope control wheels. The body of the endoscope control unit also becomes contaminated because of the right hand going from the contaminated insertion tube to the control section. Often the body of the section is contaminated as well as the wheels. It is this contamination of the control wheels and the control unit body which is addressed by this invention.

DISCLOSURE OF THE INVENTION

It is an object of the invention to provide an endoscope having easily removable control wheels so that the wheels can be either sterilized or discarded after use.

It is another object of the invention to provide a disposable bag for the control handle of an endoscope in order to prevent contamination of the control handle.

It is still another object of the invention to provide a contamination protection system for an endoscope that can be used on either conventional endoscopes or on endoscopes that are specially configured for use with a disposable endoscope sheath.

It is a further object of the invention to provide a contamination protection system for an endoscope that does not adversely effect the operability of the endoscope.

These and other objects of the invention are provided by a disposable, fluid-impermeable bag surrounding the handle of an endoscope. The bag has formed therein an aperture to allow removable control knobs to be positioned externally of the bag. The endoscope may also include a protective sheath surrounding the insertion tube, and the bag and sheath may be interconnected so that their interiors are sealed from the external environment. The bag preferably has an insertion opening formed at an end thereof that is opposite the sheath. A flexible, nonresilient member may surround at least a portion of the insertion opening to maintain the insertion opening open when the handle is inserted in the bag. The insertion opening may be sealed by a layer of pressure sensitive adhesive surrounding at least a portion of the insertion opening to maintain the insertion opening closed during use. The controls are preferably mounted on respective shafts projecting through the opening in the bag, and they are preferably rotatably interconnected so that they are removed from the handle of the endoscope as a unit.

In use, the fluid-impermeable bag is first placed around the handle of the endoscope. The control knobs are then releasably mounted on the handle externally of the bag through the aperture formed in the bag. After the endoscope has been used to perform an endoscopic procedure, the control knobs are detached from the handle and the endoscope is removed from the bag. Finally, the control knobs are decontaminated or sterilized before they are once again attached to the endoscope to perform an endoscopic procedure. If a protective sheath is used, it is placed around the insertion tube before performing the endoscopic procedure and it is removed after the procedure has been completed.

BRIEF DESCRIPTION OF THE DRAWINGS

FIG. 1 is an isometric view of an endoscope handle utilizing the inventive contamination protection system.

FIG. 2 is an isometric view of the endoscope handle of FIG. 1 showing its control wheels and braking mechanism removed.

FIG. 9 is a cross-sectional view of an alternative embodiment of a removable control wheel and braking mechanism for use with the endoscope handle of FIG. 8.

FIG. 11 is a side elevational view of an endoscope using the inventive contamination protection system in which a splatter guard is placed between the control knobs of the endoscope.

FIG. 12 is a cross-sectional view taken along the line 12—12 of FIG. 11.

BEST MODE FOR CARRYING OUT THE INVENTION

Figure 3:
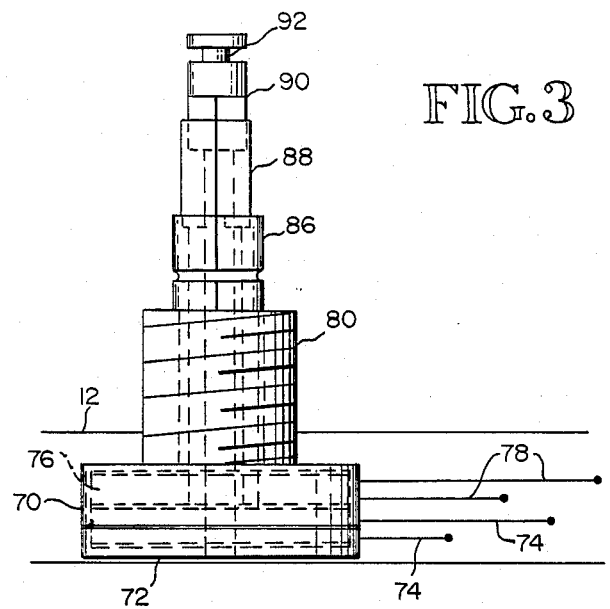
FIG. 3 is a side elevational view showing the portion of the endoscope handle of FIG. 1 on which its control wheels and braking mechanism are mounted.

The inventive endoscope 10, illustrated in FIG. 1, has the same appearance as a conventional endoscope. The endoscope includes a handle 12 having an eyepiece 14 and an elongated, flexible insertion tube 16. As is well-known in the art, the insertion tube 16 is inserted into a body cavity, and light emitting from the distal end of the insertion tube 16 illuminates tissues in the body cavity. The image viewed through the distal end of the insertion tube 16 is conveyed to the endoscope handle 12, either through an internal fiberoptic bundle or electronically from a miniature television camera mounted at the distal end of the insertion tube 16. In the embodiment illustrated in FIG. 1, the image is conveyed through the insertion tube 16 through a fiberoptic bundle and is visible through the eyepiece 14.

The insertion tube 16 also normally includes internal channels (not shown) opening at the distal end of the insertion tube 16. These tubes are used for suctioning fluids from the body cavity, for inserting air into the body cavity and for spraying water onto a lens (not shown) at the distal end of the insertion tube 16, in order to clean the lens. The suction through the suction channel of the insertion tube 16 is controlled by a suction valve 30 while the flow of air and water through the air and water channels, respectively, is controlled by a combination air/water valve 32.

When conducting an endoscopic procedure, it is necessary to manipulate the angular orientation of the distal end of the insertion tube 16. The insertion tube is manipulated in the up and down direction by rotating an up/down ("U/D") control wheel 40 in opposite directions and in the right and left directions by manipulating a right/left ("R/L") control wheel 44. As explained in greater detail below, the control wheels 40, 44 drive respective pulleys, each of which retract and pay out a pair of complementary control cables extending through the insertion tube 16 to its distal end. The control wheels 40, 44 can be frictionally locked through respective, internal braking mechanisms, as also described in greater detail below.

The inventive endoscope 10 is most advantageously used with the protective endoscope sheath described in and claimed in U.S. Pat. No. 4,646,722. The use of a protective endoscope sheath surrounding the insertion tube 16 and incorporating suction cup, air/water and biopsy channels, completely prevents contamination of the insertion tube 16. However, as explained above, it is possible for the endoscopist to contaminate handle 12 of the endoscope by grasping the contaminated outer surface of the sheath and then grasping the handle 12, such as when manipulating the control wheels 40, 44. However, in the inventive contamination protection system the handle 12, except for the eyepiece 14, is surrounded by a protective bag 50 that prevents contamination of the handle 12. The bag 50 preferably mates with a protective sheath 52 to prevent contamination of the endoscope 10 at the junction between the bag 50 and sheath 52.

The bag 50 and sheath 52 are installed on the endoscope by inserting the insertion tube 16 into the sheath 52 through an opening 54 in the bag 50. As best illustrated in FIG. 2, the control wheels 40, 44 and internal braking mechanism (not shown) are specially adapted to be removed from the handle 12 so that the control wheels 40, 44 may be mounted outside the bag 50. After the handle 12 has been inserted in the bag 50, the opening 54 is closed by suitable means such as by removing a backing strip 56 from a strip of adhesive applied to the bag so that opposite edges of the bag opening 54 adhere to each other. The control wheels 40, 44 are then mounted on the handle 12, as illustrated in FIG. 1, thereby making the endoscope 10 ready for use.

When designing a bag for an endoscope handle, one must take into consideration the two basic different types of handles used in endoscopy today. The basic difference between the handles results from the type of imaging system used in the endoscope. One uses a fiber optic imaging system and the other utilizes a video imaging system.

The fiber optic system as depicted in FIG. 1, shows an eyepiece 14 extending through insertion tube 16 allowing the endoscopist to view directly into the optical components. It is also possible to have the bag 50 cover the eyepiece 14 of the fiber optic system with a clear membrane to further isolate the endoscope handle 12. The primary reason for encouraging the design is to allow for quick and simple accessory attachment; such as cameras and teaching apparatus. It is also important to note that an endoscopist would not, under normal circumstances, touch the eyepiece 14 of his or her endoscope and hence a very low risk exists for cross contamination with this design. If one wishes to eliminate any possibility of cross contamination, an eyepiece cover must be used.

It is also important to note that in video endoscopy there is no eyepiece on the handle of the endoscope. Instead, images are reconstructed on a monitor. It is therefore unnecessary to have an eyepiece 14 extend through the bag 50. In this case, the bag 50 for the video version would be closed entirely with no extending components.

At the conclusion of an endoscopic procedure, the control wheels 40, 44 are removed from the handle 12 and sterilized in an autoclave. The handle 12 is then removed from the bag 50 through the opening 54 after the edges of the opening 54 are pulled apart, and the insertion tube 16 is removed from the sheath 52. As a result, the only portions of the endoscope 10 that become contaminated are the control wheels 40, 44. It will be understood that the control wheels 40, 44 could be placed inside the bag 50 so that the wheels 40, 44 are manipulated through the bag 50. However, placing the control wheels 40, 44 inside the bag 50 makes it very difficult to manipulate the control wheels 40, 44, particularly when they must be rotated in opposite directions.

The removable control wheels 40, 44, braking mechanisms and associated hardware are illustrated in FIGS. 3-7. With reference now to FIG. 3, a cylindrical housing 70 is mounted within the handle 12 and encloses a first pulley 72 on which right/left control cables 74 are mounted and a second pulley 76 on which up/down control cables 78 are wound. As mentioned above, the right/left control cables 74 are connected to diametrically opposite portions of the insertion tube 16 at the distal ends to control the upward and downward movement of the distal end of the insertion tube 16 responsive to the rotation of the pulley 72 in opposite directions. Similarly, the up/down control cables 78 are connected to diametrically opposite portions of the distal end of the insertion tube 16 so that the distal end of the insertion tube 16 moves down and up responsive to rotation of the pulley 76 in opposite directions.

A cylindrical, threaded, hollow stud 80 projects outwardly from the housing 70. A first shaft 86 extends through the stud 80 and is connected to the up/down pulley 76. Similarly, a second shaft 88 extends through the hollow axis of shaft 86 and is connected to the right-/left pulley 72. Finally, a nonrotating mounting pin 90 extends through the shafts 86, 88 and is anchored to a stationary portion of the housing 12. A notch 92 formed in the mounting pin 90 allows the control mechanism to be fixedly secured to the housing 12 as explained in greater detail below.

Figure 4:
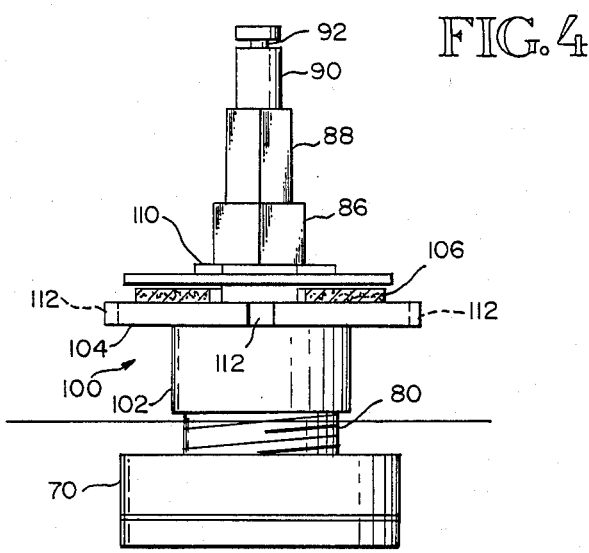
FIG. 4 is a side elevational view showing the down/up braking mechanism mounted on the endoscope handle of FIG. 1.

With reference to FIG. 4, a up/down brake includes a brake actuator member 100 having an internally threaded cylindrical portion 102 terminating in an outwardly extending flange 104. The cylindrical portion 102 is threaded onto the stud 80. An annular brake pad 106 of conventional material is mounted on the upper surface of the flange 104. Finally, a stainless steel plate 108 is retained on the up/down shaft 86 by a conventional retaining ring 110 received within an annular groove in the shaft 86. As explained in greater detail below, the shaft 86 has an octagonal shape, and the inner periphery of the plate 108 is configured to match this octagonal shape. As a result, the plate 108 and shaft 86 rotate together. A plurality of circumferentially spaced notches 112 are formed on the outer periphery of the flange 104.

Rotation of the cylindrical portion 102 and flange 104 causes the flange 104 to move inwardly and outwardly along the stud 80. Outward movement of the flange 104 forces the brake pads 106 against the brake plate to frictionally restrain rotational movement of the brake plate 108. Since the brake plate 108 is keyed to the shaft 86, rotation of the shaft 86 is restrained by the friction between the brake pads 106 and the brake plate 108. The magnitude of this frictional restraint is controlled by the rotational position of the cylindrical portion 102 and flange 104.

Figure 5:
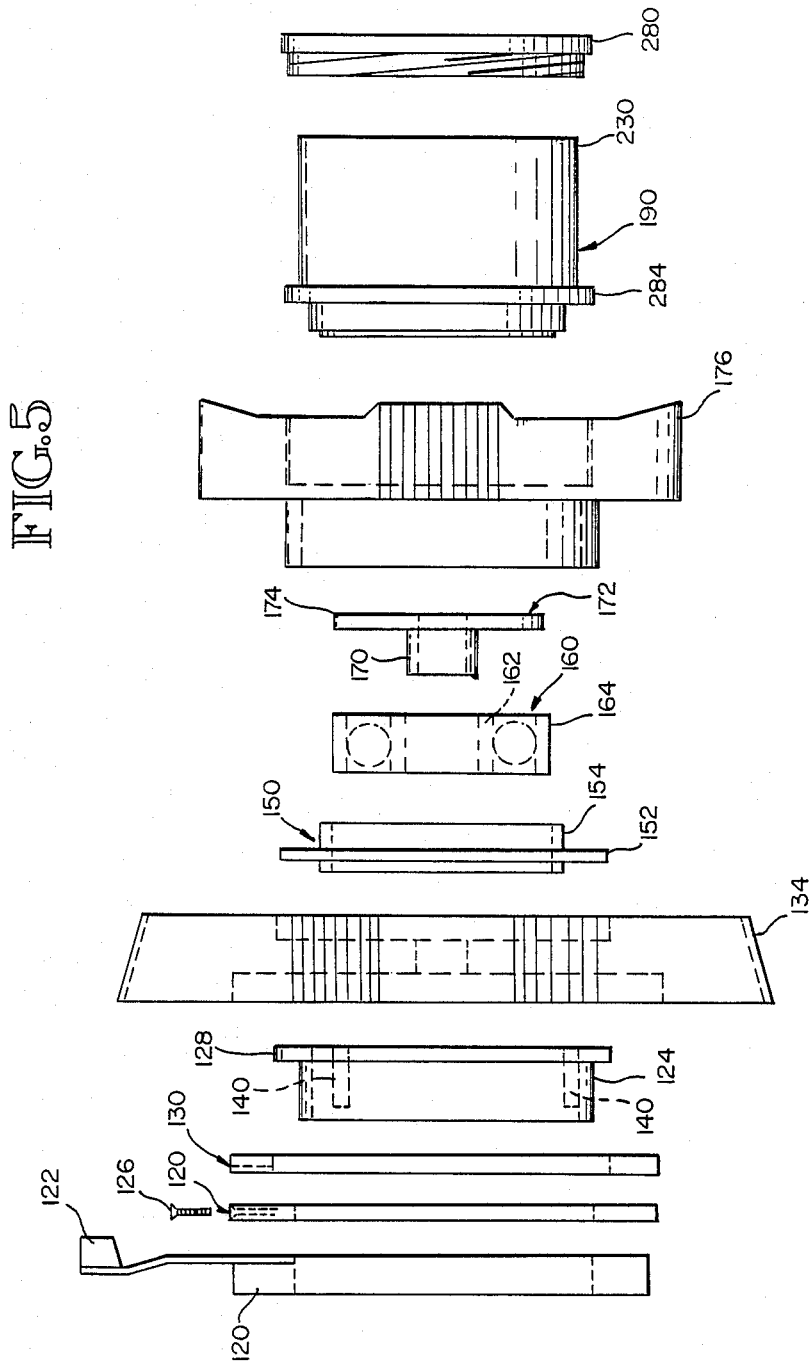
FIG. 5 is an exploded elevational view of the control wheel and braking mechanism used in the inventive contamination protection system of FIG. 1.
Figure 6:
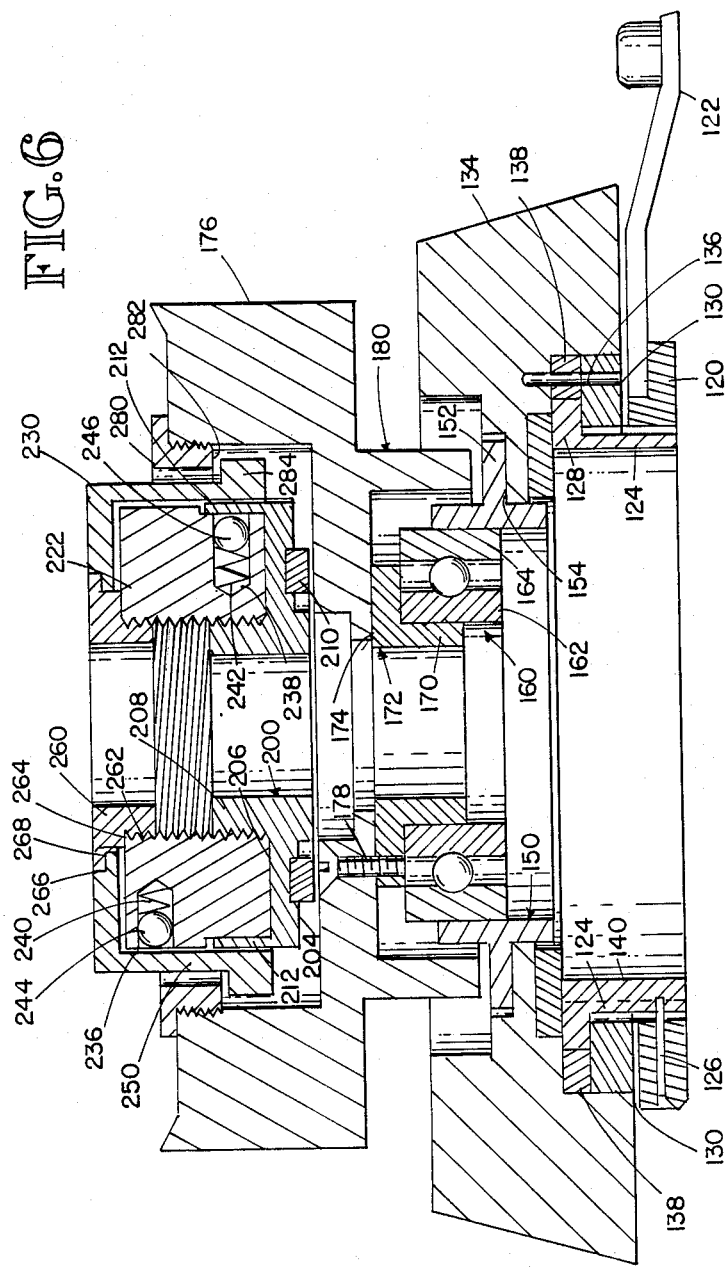
FIG. 6 is a cross-sectional view of the removable control wheel and braking mechanism used in the inventive contamination protection system of FIG. 1 shown in its assembled condition.

Referring now to FIGS. 5 and 6, a cylindrical brake coupling ring 120 having an outwardly projecting brake handle 122 is secured to a brake coupling member 124 by a plurality of circumferentially spaced screws 126 (FIG. 6). The brake coupling member 124 includes an outwardly projecting flange 128 that is captured by a retaining ring 130. The retaining ring 130 is secured to a up/down control knob 134 by a plurality of circumferentially spaced screws 136. An annular spacer 138 spaces the retaining ring 130 a slight distance from the flange 128 of the brake coupling member 124. As a result, the retaining ring 130 secures the brake coupling member 124 to the up/down control knob 134, but allows the brake coupling member 124 to rotate with respect to the up/down control knob 134. The brake coupling member 124 includes a plurality of cogs 140 projecting axially toward the handle 12. The cogs 140 are received by the respective notches 112 in the flange 104 of the brake actuator member 100 (FIG. 4). As a result, when the control wheel and braking mechanism illustrated in FIG. 6 are inserted onto the up/down braking mechanism illustrated in FIG. 4, rotation of the brake handle 122 rotates the brake actuator member 100 through the brake coupling member 124. At the same time, rotation of the up/down control knob 134 rotates the up/down shaft 86 (FIG. 4) since the internal bore of the up/down control knob 134 is keyed to the hexagonal shape of the shaft 86.

The up/down control knob 134 is rotatably secured to other components of the control wheel and brake mechanism through a mounting member 150 having an outwardly projecting flange 152 surrounding a cylindrical portion 154. The flange 152 is secured to the outer face of the inner portion of the up/down control knob 134 by suitable means, such as a conventional adhesive. A ball bearing assembly 160 having inner and outer races 162, 164, respectively, is mounted in the mounting member 150 by securing the outer surface of the outer race 164 to the inner surface of the cylindrical portion 154 of the mounting member 150.

The inner surface of the inner race 162 is secured around the outer surface of a cylindrical portion 170 of a second mounting member 172 by suitable means, such as a conventional adhesive. The mounting member 172 includes an outwardly projecting flange 174 that is secured to a right/left control knob 176 by a plurality of circumferentially spaced screws 178. The right/left control knob 176 is thus rotatably secured to the up/-down control knob through the mounting member 150, ball bearing assembly 160 and mounting member 172. The right/left control knob 176 includes an integrally formed inwardly depending cylindrical flange 180 that surrounds the ball bearing assembly 160. A square aperture formed at the center of the right-left control knob 176 is key to the square shape of the right/left control shaft 88. A hexagonal aperture formed at the center of the up/down control knob 134 is key to the hexagonal shape of the up/down control shaft 86 so that rotation of the up/down control knob 134 rotates the up/down pulley 76 through the up/down control shaft 86.

Figure 7:
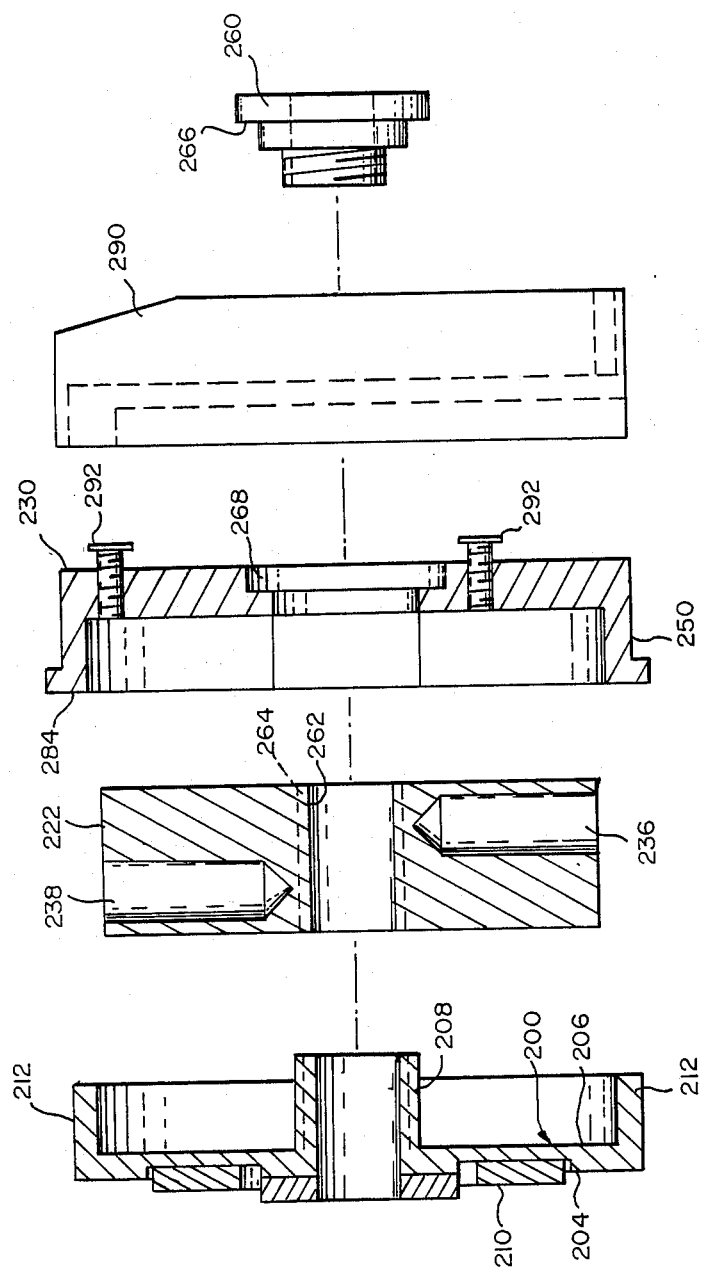
FIG. 7 is an exploded cross-sectional view of the right/left brake assembly used in the control wheel and braking mechanism of FIGS. 5 and 6.

A right/left brake assembly 190 is mounted on top of the right/left control knob 176. The right/left brake assembly is best illustrated in FIGS. 6 and 7. The right-/left brake assembly includes a braking plate 200 having an inner surface 204, an outer surface 206, and a cylindrical boss 208. An annular brake pad 210 of frictional braking material is secured to the inner surface 204 of the braking plate 200. The braking plate 200 also includes outer, axially extending flange 212 having a plurality of circumferentially spaced notches formed on its inner surface, the purpose of which is explained below. The braking plate 200 is keyed to the square mounting pin 90 so that the braking plate 200 cannot rotate.

The boss 208 of the braking plate 200 is externally threaded, and these threads mate with internal threads lining the border of a coupling member 222. The coupling member 222 is, in turn, enclosed by a brake adjusting knob 230. A pair of radial recesses 236, 238 are formed in the coupling member 222 at axially spaced locations. The recesses 236, 238 receive respective compression springs 240, 242 which outwardly bias respective ball bearings 244, 246. Ball 246 is biased against the inner surface of flange 212, which, it will be recalled, has formed therein a plurality of circumferentially spaced notches adapted to receive the ball 246. Similarly, the ball 236 is biased against the inner surface of a downwardly extending flange 250 forming part of the brake adjusting knob 230. The inner surface of the flange 250 likewise has formed therein a plurality of circumferentially spaced grooves adapted to receive the ball 244. The spring constant of the spring 242 is lower than the spring constant of the spring 240, the reason for which is explained below.

The brake adjusting knob 230 is rotatably secured to the coupling member 222 by an annular nut 260 having external threads 262 threaded into the internal threads of the coupling member 222. The nut 260 is threaded into the coupling member 222 until a stepped shoulder 264 forcibly contacts the upper end of the coupling member 260. In this position, a second step shoulder 266 of the nut 260 is spaced slightly from an inwardly stepped recess 268 of the brake adjustment knob 230 so that the brake adjustment knob 230 is free to rotate. The right/left braked assembly is adjusted by rotating the brake adjustment knob 230. The rotation of the brake adjustment knob 230 is then coupled to the coupling member 222 through the ball bearing 244 and notches formed on the interior surface of the flange 250 so that the coupling member 222 rotates with the brake adjustment knob 230. Insofar as the spring 242 has a lighter spring constant than the spring constant of the spring 240, the ball bearing 246 mating with the notches formed in the flange 212 of the stationary braking plate 200 does not prevent rotation of the coupling member 222. Instead, the ball bearing 246 and notches maintain the position of the coupling member 222 until a rotational force greater than a predetermined value is applied to the brake adjustment knob 230. Rotation of the coupling member 222 applies a downward axial force to the braking plate 200 through the mating threads of the coupling member 222 and braking plate 200, thereby forcing the brake pad 210 against the upper surface of the up/down control knob 176 to increase the frictional braking force. After the braking force has been adjusted up to a predetermined value, the ball bearing 244 and notches formed in the flange 250 are no longer capable of coupling the rotational force of the brake adjustment knob 220 to the coupling member 222, thereby allowing the brake adjustment knob 230 to rotate with respect to the coupling member 222. The spring 240 and ball bearing 244 thus serve as a clutch to prevent excessive right-/left brake adjustments.

The right/left brake assembly 190 is rotatably secured within the right/left control knob 176 by an annular ring 280 which is threaded into internal threads formed in the right/left control knob 176. The lower end 282 of the ring contacts an outwardly extending peripheral flange 284 formed in the brake adjustment knob 230 to prevent axial movement of the brake adjustment knob 230, coupling member 222 and braking plate 200.

It is apparent from an examination of FIG. 6 that virtually all of the external components of the control and brake mechanisms of the endoscope are removable as a unit. The only components of the control and braking mechanisms that remain on the handle of the endoscope are the control shafts 88, 86, the threaded boss 80 and the mounting pin 90 (see FIG. 3). However, all of these components are shielded during use by the removable components illustrated in FIG. 6. As a result, the protective bag 50, coupled with the removal and sterilization of the control and braking mechanism after each use, prevents contamination of the endoscope 10.

With reference to FIGS. 3 and 7, the entire control and brake mechanism illustrated in FIG. 6 is secured to the handle of the endoscope by a clip member 290 (FIG. 7) fitting onto a pair of studs 292 projecting from the brake adjustment knob 230. An internal elongated slot and recess formed in the clip member 290 receives the end of the mounting pin 90 as the clip member 290 slides onto the studs 292. The clip member 290 thus rotates with the brake adjustment knob 230 and, in cooperation with the notch 92 formed in the mounting pin 90, releasably secures the clamp and brake mechanism to the handle of the endoscope.

Figure 8:
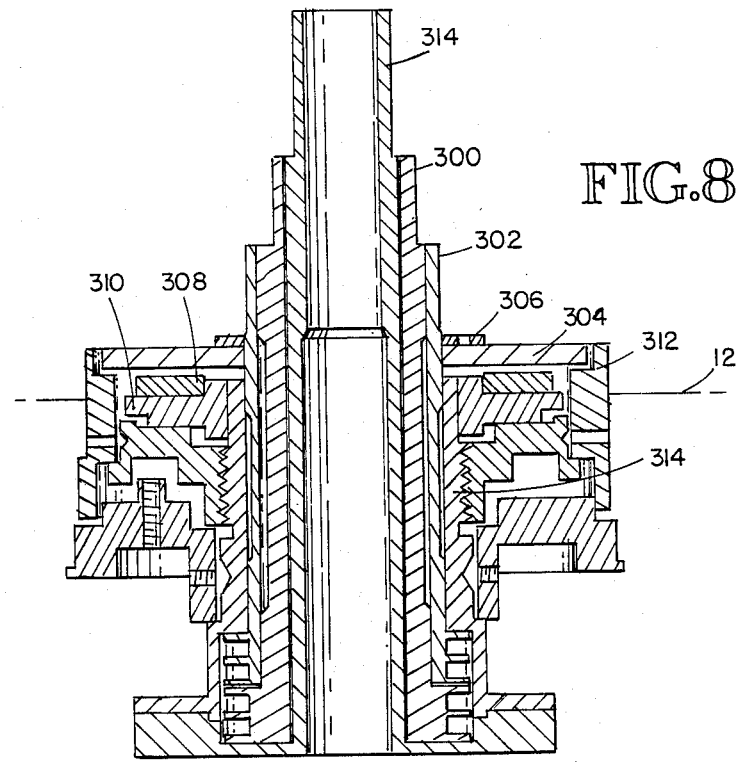
FIG. 8 is a cross-sectional view of an alternative embodiment of the portion of an endoscope handle on which an alternative embodiment of a removable control wheel and braking mechanism is mounted.
Figure 10:
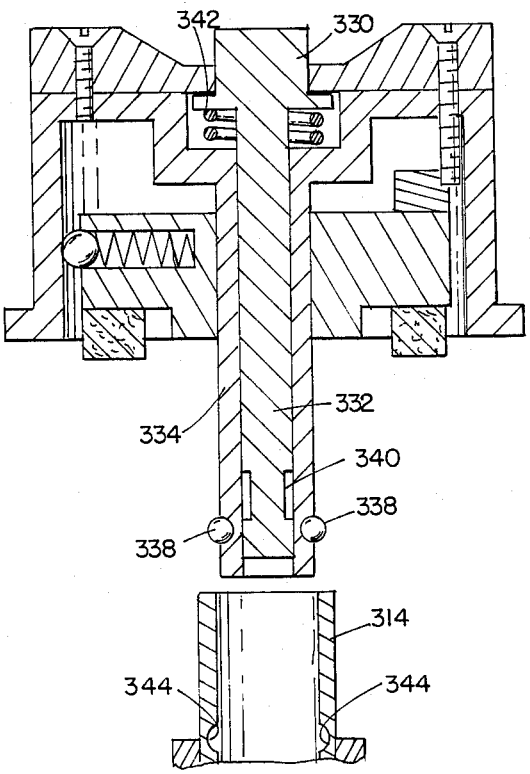
FIG. 10 is a partial exploded cross-sectional view of the alternative embodiment of the removable control wheel and braking mechanism of FIG. 9 and the endoscope handle of FIG. 8.

An alternative embodiment of a removable control and braking mechanism is illustrated in FIGS. 8-10. With reference to FIG. 8, the portions of the mechanism fixedly mounted in the handle 12 of the endoscope 10 is basically the same as in the embodiment of FIGS. 3-7. The major components of the embodiment of FIG. 8 include concentric right/left and up/down control shafts 300, 302, a braking plate 304 retained in position on shaft 302 by a retaining ring 306 and an annular brake pad 308 of frictional braking material mounted on a brake actuating plate 310 and connected to a brake actuating member 312 so that the actuating plate 310 and actuating member 312 rotate as a unit. As explained in greater detail below, the brake actuating member 312 is coupled to a removable portion of the control and braking mechanism in order to rotate the actuating member 312. The brake actuating plate 310 is mounted on a threaded boss 314 so that rotation of the brake actuating plate unscrews the actuating plate 310 from the boss 314. As a result, rotation of the brake actuating member 312 raises the brake actuating plate 310, thereby forcing the frictional braking material 308 against the plate 304. The plate 304 is keyed to the control shaft 302 so that the friction between the material 308 and the plate 304 restricts rotation of the shaft 302. A stationary support shaft 314 projects coaxially through the shafts 300, 302. As explained in greater detail below, the removable portions of the control and braking mechanism are mounted on the shaft 314.

With reference now to FIG. 9, most of the removable components of the control and braking mechanism in the embodiment of FIGS. 8-10 are virtually identical to the components in the embodiment of FIGS. 3-7. In the interest of brevity, these virtually identical components will be given the same reference numerals in both embodiments, and they will not be separately explained.

The embodiment of FIGS. 8-10 differs from the embodiment of FIGS. 3-7 primarily in the manner in which the removable control and braking mechanism is releasably secured to the handle 12 of the endoscope 10. In the embodiment of FIGS. 8-10, an end plate 320 is secured to the end of the brake actuating knob 220 by a pair of screws 322. A release button 330 is mounted in the end plate 320 at the end of an elongated release member 332. The release member 332 is slidably mounted in a coupling shaft 334 having a pair of apertures 336 receiving respective ball bearings 338. A recessed portion 340 of the release member 332 is positioned adjacent the ball bearings 338 when the release button 330 is pressed. When the recess portion 340 is adjacent the ball bearings 338, the ball bearings can move inwardly. At all other times, the ball bearings 338 are maintained in their outer position by the full diameter of the release member 332.

With reference to FIG. 10, the coupling shaft 334 is inserted into the support shaft 314 after the release button 330 has been pressed to allow the locking balls 338 to move inwardly into the recess portion 340 of the release member 332. The release button 330 is biased upwardly by a compression spring 342. As a result, when the locking balls 338 are positioned adjacent an annular groove 334 formed in the interior of the support shaft 314, the locking balls 338 are forced outwardly into the groove 334 by the upward movement of the release button 330. When the control and brake mechanism is to be removed, the release button 330 is pressed, thereby allowing the locking balls 338 to move inwardly into the recess portion 340. The removable portion of the control and braking mechanism is then removed from the handle by sliding the coupling shaft 334 out of the support shaft 314.

Typically, an endoscopist uses his or her right hand to advance and retract the endoscopest by manipulating the insertion tube 16 directly. The right hand then becomes contaminated from debris from the insertion tube 16. The same hand would more than likely be used to control the right/left control knob 44 of the endoscope, thereby causing direct contamination from the insertion tube debris. With reference to FIGS. 11 and 12, these contaminants can be prevented from traveling further onto the endoscope hand piece 12, by using a guard 390 in the form of a thin circular plate between the up/down and the right/left control knob 44. The diameter of the guard 390 should be substantially larger than the diameter of the right/left control knob 40 to prevent either the right/left control knob 40 from being manipulated by the right hand or the up/down control knob 44 from being manipulated by the left hand. The guard 390 prevents the left hand of the endoscopist from manipulating the right/left control knob 44 or inadvertently contacting the right/left control knob 44. Similarly, the guard 390 would prevent the endoscopist's right hand from inadvertently contacting the up/down control knob 40 or manipulating the up/down control knob 40.

We claim:

1. A system for protecting an endoscope from external contamination, said endoscope having a handle, an elongated insertion tube extending from said handle to a distal end, a set of control cables for controlling the angular orientation of the distal end of said insertion tube, and control knobs applying control forces to said control cables, said system comprising:
  a fluid-impermeable bag surrounding the handle of said endoscope, said bag having an aperture formed therein to allow said control knobs to be positioned externally of said bag; and
  fastening means for allowing said control knobs to be detached from said handle so that said control knobs can be decontaminated between uses of said endoscope.

2. The protection system of claim 1 wherein said endoscope further includes a protective sheath surrounding said insertion tube, and wherein said bag and sheath are interconnected and their interiors are sealed from the external environment so that said bag and sheath isolate said endoscope from external contamination.

3. The protection system of claim 2 wherein said bag has an insertion opening formed at an end thereof that is opposite said sheath.

4. The protection system of claim 3 wherein said bag further includes a flexible, nonresilient member surrounding at least a portion of said insertion opening to maintain said insertion opening open when said handle is inserted in said bag.

5. The protection system of claim 3 wherein said bag further includes a layer of pressure-sensitive adhesive surrounding at least a portion of said insertion opening to maintain said insertion opening closed in use after said handle has been inserted in said bag.

6. The protection system of claim 1 wherein said controls are removably mounted on respective shafts and wherein said shafts project through said opening in said bag.

7. The protection system of claim 1 wherein said set of cables include a pair of up/down cables for controlling the vertical orientation of the distal end of said insertion tube, a pair of right/left cables for controlling the horizontal orientation of the distal end of said insertion tube, and concentric up/down and right/left control shafts driving said up/down and right/left cables, respectively, and wherein said control knobs include a up/down control knob removably engaging said up/down control shaft and a right/left control knob removably engaging said right/left control knob, and wherein said system further includes interconnecting means for restricting relative axial movement between said control knobs while permitting free relative rotational movement between said control knobs, whereby said control knobs can independently drive said up/down and right/left control cables but are removed from and installed on said handle as a unit.

8. The protection system of claim 7 wherein said endoscope further includes up/down braking means for restraining rotation of said up/down control shaft and right/left braking means for restraining rotation of said right/left control shaft, and wherein said interconnecting means restricts relative axial movement of said braking means with respect to each other and to said control knobs while permitting said braking means to operate independently of each other so that said braking means and said control knobs are removed from and installed on said handle as a unit.

9. The system of claim 1 wherein said control knobs include a right/left control knob and an up/down control knob, said system further including a guard plate positioned between said right/left control knob and said up/down control knob, said guard plate having a minimum transverse dimension that is substantially larger than the diameter of the control knob having the largest diameter.

10. An endoscope having a handle and an elongated insertion tube extending from said handle to a distal end, said endoscope comprising:
  a set of up/down cables for controlling the vertical orientation of the distal end of said insertion tube;
  a set of right/left cables for controlling the horizontal orientation of the distal end of said insertion tube;
  a first control shaft operating one set of said control cables;
  a second control shaft operating the other set of said control cables, said second control shaft being concentrically positioned within said first control shaft;
  an elongated support projecting from said handle, said support being concentrically positioned within said second control shaft;
  a threaded stud surrounding said control shafts;
  a first brake actuating member threaded onto said stud, said brake actuating member having an annular layer of frictional braking material mounted on an external surface of said brake actuating member and surrounding said stud;

an annular brake plate surrounding said threaded stud adjacent the frictional braking material on said brake actuating member, said brake plate being keyed to said first control shaft so that said brake plate and said shaft rotate together, whereby rotation of said brake actuating member in one direction causes said actuating member to move toward said brake plate, thereby forcing said layer of frictional braking material against said brake plate with increasing force in order to restrain rotation of said first control shaft;

a first control knob releasably attached to said first control shaft so that rotation of said first control knob rotates said first control shaft;

a brake actuating lever rotatably mounted on said first control knob, said brake actuating lever being releasably coupled to said brake actuating member;

a second control knob releasably attached to said second control shaft so that rotation of said second control knob rotates said second control shaft, said second control knob being rotatably mounted on said first control knob, said second control shaft further including an annular braking surface concentrically surrounding said elongated support;

a second brake actuating member rotatably secured to said second control knob, said second brake actuating member having a second annular layer of frictional braking material positioned closely adjacent the braking surface of said second control knob, said brake actuating member further including adjusting means for causing said second brake actuating member to move in one direction toward said layer of frictional braking material, thereby forcing said layer of frictional braking material against the braking surface of said second control knob with increasing force in order to restrain rotation of said second control shaft; and fastening means for releasably and rotatably securing said second brake actuating member to said elongated support to secure said control knobs, said brake actuating lever and said second brake actuating member to the handle of said endoscope while allowing said control knobs, said brake actuating lever and said second brake actuating member to be removed from said endoscope handle as a unit.

11. The endoscope of claim 10 wherein said second brake actuating member includes a brake adjusting knob rotatably mounted on said second control knob, a brake disk nonrotatably mounted on said elongated support, said brake disk having said second annular layer of frictional braking material mounted thereon adjacent said second control knob, and a coupling member positioned between said brake adjusting knob and said said brake disk and connected to said brake adjusting knob, and wherein said adjusting means includes threads formed on said coupling member and mating with threads formed on said brake disk so that rotation of said coupling member in one direction moves said brake disk axially toward said second control knob, thereby causing said second layer of frictional braking material to engage said second control knob with increasing force.

12. The endoscope of claim 11 wherein said brake adjusting knob is connected to said coupling member through a first coupling mechanism that allows said adjusting knob to rotate with respect to said coupling member when the torque that said brake adjusting knob exerts on said coupling member exceeds a predetermined value, thereby limiting the maximum braking force to which said second brake actuating member can be adjusted.

13. The endoscope of claim 12 wherein said coupling member is connected to said brake plate through a second coupling mechanism that allows said coupling member to rotate with respect to said brake plate when the torque that said coupling member exerts on said brake plate exceeds a second predetermined value, thereby preventing the adjustment of said second brake actuating member unless a torque of at least said second predetermined value is applied to said brake adjusting knob, said first predetermined value being larger than said second predetermined value so that said second coupling mechanism releases to allow said coupling member to rotate with respect to said brake plate before said first coupling mechanism releases to allow said coupling member to remain stationary as said brake adjusting knob is rotated.

14. The endoscope of claim 10 wherein said elongated support is formed by a hollow shaft projecting from said handle within said first and second control shafts, and wherein said fastening means includes a second shaft rotatably secured to said control knobs and extending along the axis thereof, said second shaft extending into the hollow shaft forming said elongated support, said endoscope further including fastening means releasably securing said second shaft within said hollow shaft.

15. The endoscope of claim 10, further including a guard plate positioned between said right/left and said up/down control knob, said guard plate having a minimum tansverse dimension that is substantially larger than the diameter of the largest diameter of said control knob.

16. A method of protecting an endoscope from external contamination, said endoscope having a handle, an elongated insertion tube extending from said handle to a distal end, a set of control cables for controlling the angular orientation of the distal end of said insertion tube, and control knobs applying control forces to said control cables, said method comprising:

placing a fluid-impermeable bag around the handle of said endoscope, said bag having an aperture formed therein to allow said control knobs to be positioned externally of said bag;

attaching control knobs to said handle externally of said bag;

using said endoscope to perform an endoscopic procedure;

detaching said control knobs from said handle;

removing said endoscope from said bag; and decontaminating or sterilizing said control knobs before they are once again attached to said endoscope to perform an endoscopic procedure.

17. The method of claim 16, further including the steps of placing a protective sheath around said insertion tube before performing said endoscopic procedure and removing said insertion tube from said sheath after said procedure has been completed.

18. The method of claim 17, further including the step of interconnecting said bag and sheath so that the interiors of said bag and sheath are sealed from the external environment, whereby said bag and sheath isolate said endoscope from external contamination.

* * * * *